United States Patent
Weerawarna et al.

(10) Patent No.: US 6,852,860 B2
(45) Date of Patent: Feb. 8, 2005

(54) METHOD FOR MAKING PIPERIDONE KETALS USING POLYPHOSPHORIC ACID

(75) Inventors: S. Ananda Weerawarna, Seattle, WA (US); Richard A. Jewell, Tacoma, WA (US)

(73) Assignee: Weyerhaeuser Company, Federal Way, WA (US)

( * ) Notice: Subject to any disclaimer, the term of this patent is extended or adjusted under 35 U.S.C. 154(b) by 0 days.

(21) Appl. No.: 10/390,354

(22) Filed: Mar. 14, 2003

(65) Prior Publication Data

US 2004/0192920 A1 Sep. 30, 2004

(51) Int. Cl.[7] ................ C07D 221/20; C07D 491/113
(52) U.S. Cl. ........................................ 546/16; 546/19
(58) Field of Search ..................... 546/16, 19

(56) References Cited

U.S. PATENT DOCUMENTS 6,524,348 B1    2/2003   Jewell et al.

FOREIGN PATENT DOCUMENTS

| EP | WO 01/23309 | 4/2001 |
| JP | 55041432 | 3/1980 |
| JP | 56-138189 | * 10/1981 |

OTHER PUBLICATIONS

Meskens F, "Methods for the Preparation of Acetals," Janssen Chimica 1(1) 1983, pp. 10–17.

* cited by examiner

Primary Examiner—Rita Desai
(74) Attorney, Agent, or Firm—Christensen O'Connor Johnson Kindness PLLC

(57) ABSTRACT

A method for making piperidone ketals by condensing a suitable alcohol with a piperidone in the presence of polyphosphoric acid.

18 Claims, 1 Drawing Sheet

METHOD FOR MAKING PIPERIDONE KETALS USING POLYPHOSPHORIC ACID

FIELD OF THE INVENTION

The present invention relates to a method for making piperidone ketals using polyphosphoric acid.

BACKGROUND OF THE INVENTION

A ketal can be prepared by condensing an alcohol with a ketone. The ketal forming reaction is often carried out in a solvent such as benzene or toluene in the presence of an acid catalyst such as p-toluenesulfonic acid. The ketal forming reaction is typically driven to completion by azeotropic removal of water from the reaction mixture as the water is formed by the condensation of the diol with the ketone. One drawback with such a synthetic method is the need to remove water from the reaction mixture as it is formed in order to drive the reaction to completion. Another drawback is that, in order to remove the water from the reaction mixture, the solvent must be capable of forming an azeotrope with water and, typically, such solvents include benzene and toluene, which are considered to be hazardous and require certain handling precautions.

There exists a need for improved synthetic methods that readily provide ketals without the drawbacks associated with the azeotropic removal of water from the reaction mixture. The present invention seeks to fulfill these needs and provides further related advantages.

SUMMARY OF THE INVENTION

In one aspect of the invention, a method for making piperidone ketals is provided. In the method a piperidone is condensed with an alcohol in the presence of polyphosphoric acid.

In another aspect, the invention provides piperidone ketals.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE PREFERRED EMBODIMENT

Figure 1:
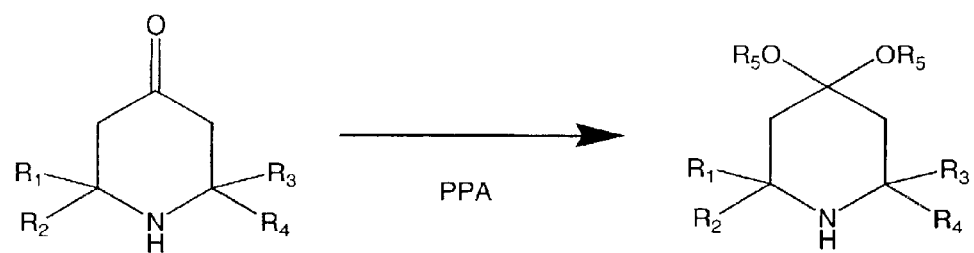
FIG. 1 is a schematic illustration of a representative method of the invention for preparing a piperidone ketal; a 2,2,6,6-tetrasubstituted-4-piperidone ketal by the condensation of a 2,2,6,6-tetrasubstituted-4-piperidone with an alcohol in the presence of polyphosphoric acid (PPA).

The present invention provides a method for making piperidone ketals by condensing a suitable alcohol with a piperidone in the presence of polyphosphoric acid. Polyphosphoric acid effectively removes water from the condensation reaction mixture as it is formed thereby driving the condensation reaction to completion.

A schematic illustration of the conversion of a representative piperidone to the corresponding piperidone ketal according to the method of the invention is shown in FIG. 1.

Referring to FIG. 1, suitable piperidones include $R_1$–$R_4$. $R_1$–$R_4$ can be C1–C6 straight-chain or branched alkyl groups, for example, methyl, ethyl, propyl, butyl, pentyl, or hexyl groups. Alternatively, $R_1$ and $R_2$ taken together can form a five- or six-carbon cycloalkyl group, and $R_3$ and $R_4$ taken together can form a five- or six-carbon cycloalkyl group. The cycloalkyl group can be further substituted with, for example, one or more C1–C6 alkyl groups or other substituents. In addition to $R_1$–$R_4$, the product ketals include $R_5$, which can be a C1–C6 straight-chain or branched alkyl group. Alternatively, the $R_5$ substituents taken together can form a five- or six-membered ring. The ring can be further substituted with, for example, one or more C1–C6 alkyl groups or other substituents.

In one embodiment, the $R_5$ substituents taken together form a two-carbon chain (e.g., —$CH_2CH_2$—), and the ketal is an ethylene ketal. In another embodiment, the $R_5$ substituents taken together form a three-carbon chain (e.g., —$CH_2CH_2CH_2$—), and the ketal is a propylene ketal. As noted above, substitution of the two- or three-carbon chain is possible.

Suitable piperidones useful in the invention include piperidones illustrated in FIG. 1 and having substituents $R_1$–$R_4$ as described above. In one embodiment, the piperidone is 2,2,6,6-tetramethyl-4-piperidone.

Suitable alcohols useful in the invention include C1–C6 alcohols, diols having two or three carbon atoms between the alcohol groups, and polyols having two or three carbon atoms between the alcohol groups. Suitable C1–C6 alcohols include methanol, ethanol, propanols (i.e., n-propanol and isopropanol), butanols (i.e., n-butanol, s-butanol, and t-butanol), pentanols (e.g., neopentanol), and hexanols. Suitable diols include ethylene glycol and propylene glycol. Suitable polyols include glycerol. In one embodiment, the glycol is ethylene glycol. Alkyl and aryl substituted glycols and polyols may also be used.

In the method, polyphosphoric acid is present in an amount sufficient to remove water formed in the condensation reaction from the reaction mixture. In the method, the $H_3PO_4$ equivalence relative to ketone is from about 1.5 to about 20. Polyphosphoric acid has an $H_3PO_4$ equivalence of 115%.

The reaction of the piperidone and alcohol in the presence of polyphosphoric acid can be carried out neat or in a solvent. In one embodiment, the reaction is carried out using excess alcohol (e.g., diol or polyol) or excess ketone (e.g., liquid ketone at reaction temperature).

The reaction of the piperidone and alcohol in the presence of polyphosphoric acid can be carried out at a temperature in the range from about 50° C. to about 200° C.

A representative procedure for preparing a piperidone ketal using polyphosphoric acid is described in Example 1 and illustrated in FIG. 1. Example 1 describes the preparation of 2,2,6,6-tetramethyl-4-piperidone ethylene ketal by the condensation of 2,2,6,6-tetramethyl-4-piperidone with ethylene glycol. Referring to FIG. 1, for this example, $R_1$–$R_4$ are methyl, and substituents $R_5$ taken together are —$CH_2CH_2$—. In addition to 4-piperidone ethylene ketal, other ketals, for example, 4-piperidone propylene ketal and 4-piperidone glyceryl ketal can be made by the method.

The product ketals can used in processes for preparing carboxylated cellulose fibers. The use of the nitroxide of 2,2,6,6-tetramethyl-4-piperidone ethylene ketal in a carboxylation process is described in WO 01/29309, entitled "Method of Making Carboxylated Cellulose Fibers and Products of the Method". The nitroxide is prepared from 2,2,6,6-tetramethyl-4-piperidone ethylene ketal. The cellulose carboxylation method is a two-step method: cellulose oxidation followed cellulose stabilization. In the method, the nitroxide of 2,2,6,6-tetramethyl-4-piperidone ethylene ketal is used as a primary oxidant of the cellulose fiber.

In the cellulose oxidation, the nitroxide is converted to an oxammonium salt, which after cellulose oxidation, is reduced to the corresponding hydroxylamine compound. In the method, a secondary oxidant (e.g., a water soluble hypochlorite compound such as sodium hypochlorite)

re-oxidizes the hydroxylamine compound to the nitroxide, the primary oxidant. Because the primary oxidant is regenerated in the method, only small amounts of the nitroxide (or hydroxylamine) are required; the secondary oxidant is depleted. The method provides for the selective oxidation of cellulose: the primary hydroxyl group located at C-6 of the anhydroglucose moiety of cellulose (i.e., C-6 OH) is preferentially oxidized to a carboxylic acid group (i.e., C-6 $CO_2H$).

In addition to introducing carboxylic acid substituents, the cellulose oxidation also introduces aldehyde and ketone groups into the cellulose. Because aldehyde and ketone groups are known to cause cellulose degradation, these substituents are reduced in the stabilization step to maintain cellulose degree of polymerization (i.e., maintain cellulose polymer length). In the stabilization step, the oxidized cellulose is treated with a reducing agent. Suitable reducing agents include alkali metal borohydrides (e.g., sodium borohydride).

The carboxylated fiber prepared by the method is highly advantageous as a papermaking furnish, either by itself or in combination with conventional fiber. The following example is provided for the purpose of illustrating, not limiting, the present invention.

Representative Method for Making a Piperidone Ketal Using Polyphosphoric Acid: 2,2,6,6-Tetramethyl-4-piperidone Ethylene Ketal In this example, a representative method for making a piperidone ketal using polyphosphoric acid is described.

Ethylene glycol (48.0 g, 773.3 mmol) and polyphosphoric acid (11.0 g, 132 mmol) (Aldrich Chemical Co., Milwaukee, Wis.) were added to 2,2,6,6 tetramethyl-4-piperidone (6.0 g, 38.6 mmol) in a 300 mL round bottomed flask and heated at 65° C. under nitrogen for 6 hours with stirring.

The reaction mixture was cooled and adjusted to alkaline pH with the addition of saturated aqueous sodium carbonate solution. The mixture was placed in a separating funnel and extracted with 300 mL chloroform. The chloroform solution was washed twice with 150 mL of saturated aqueous sodium carbonate solution and twice with 100 mL of de-ionized water. The resulting chloroform solution was dried over anhydrous sodium sulfate, filtered, evaporated to dryness using a rotary evaporator, and dried in vacuo to provide 2,2,6,6-tetramethyl-4-piperidone ethylene ketal as a liquid (6.85 g, 88%).

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A method for making a piperidone ketal, comprising condensing an alcohol with a piperidone in the presence of polyphosphoric acid.

2. The method of claim 1, wherein the piperidone has the formula:

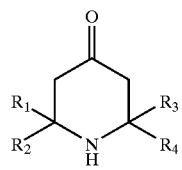

wherein $R_1$–$R_4$ are at least one of a C1–C6 straight-chain alkyl group or a branched C1–C6 alkyl group, or $R_1$ and $R_2$ taken together is a five- or six-carbon cycloalkyl group, or $R_3$ and $R_4$ taken together is a five- or six-carbon cycloalkyl group.

3. The method of claim 1, wherein the piperidone is 2,2,6,6-tetramethyl-4-piperidone.

4. The method of claim 1, wherein the polyphosphoric acid is present in an amount sufficient to remove water formed in the condensation reaction from the reaction mixture.

5. The method of claim 1, wherein the alcohol is a glycol.

6. The method of claim 1, wherein the alcohol is glycerol.

7. The method of claim 1, wherein the alcohol is at least one of ethylene glycol or propylene glycol.

8. The method of claim 1, wherein condensing the alcohol with the piperidone comprises heating to a temperature in the range from about 50° C. to about 200° C.

9. A method for making a 2,2,6,6-tetrasubstituted-4-piperidone ketal, comprising condensing an alcohol with a 2,2,6,6-tetrasubstituted-4-piperidone in the presence of polyphosphoric acid.

10. The method of claim 9, wherein the piperidone has the formula:

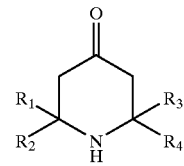

wherein $R_1$–$R_4$ are at least one of a C1–C6 straight-chain alkyl group or a branched C1–C6 alkyl group, or $R_1$ and $R_2$ taken together is a five- or six-carbon cycloalkyl group, or $R_3$ and $R_4$ taken together is a five- or six-carbon cycloalkyl group.

11. The method of claim 9, wherein the piperidone is 2,2,6,6-tetramethyl-4-piperidone.

12. The method of claim 9, wherein the polyphosphoric acid is present in an amount sufficient to remove water formed in the condensation reaction from the reaction mixture.

13. The method of claim 9, wherein the alcohol is a glycol.

14. The method of claim 9, wherein the alcohol is glycerol.

15. The method of claim 9, wherein the alcohol is at least one of ethylene glycol or propylene glycol.

16. The method of claim 9, wherein condensing the alcohol with the piperidone comprises heating to a temperature in the range from about 50° C. to about 200° C.

17. A method for making 2,2,6,6-tetramethyl-4-piperidone ethylene ketal, comprising condensing ethylene glycol with 2,2,6,6-tetramethyl-4-piperidone in the presence of polyphosphoric acid.

18. A method for making 2,2,6,6-tetramethyl-4-piperidone ethylene ketal, comprising condensing at least one of propylene glycol or glycerol with 2,2,6,6-piperidone in the presence of polyphosphoric acid.

* * * * *